United States Patent [19]

Stevens et al.

[11] Patent Number: 4,695,669
[45] Date of Patent: Sep. 22, 1987

[54] PROCESS FOR PROPYLENE DIMERIZATION

[75] Inventors: James C. Stevens; William A. Fordyce, both of Midland, Mich.

[73] Assignee: The Dow Chemical Company, Midland, Mich.

[21] Appl. No.: 902,740

[22] Filed: Sep. 2, 1986

[51] Int. Cl.$^4$ .......................... C07C 2/10; C07C 2/26
[52] U.S. Cl. .................................. 585/511; 502/117; 585/530
[58] Field of Search ............... 585/510, 511, 530, 512; 502/117

[56] References Cited

U.S. PATENT DOCUMENTS

| | | | |
|---|---|---|---|
| 2,968,681 | 1/1961 | O'Connor et al. | 585/267 |
| 2,986,588 | 5/1961 | Schramm | 585/511 |
| 3,095,461 | 6/1963 | Wilkes | 585/530 |
| 3,152,157 | 8/1964 | Shapiro et al. | 556/58 |
| 3,175,020 | 3/1965 | Wilkes | 585/516 |
| 3,251,895 | 5/1966 | Wilkes | 585/511 |
| 3,414,633 | 12/1968 | Stapp | 585/512 |
| 3,488,367 | 1/1970 | Fischer et al. | 534/11 |
| 3,536,632 | 10/1970 | Kroll | 502/107 |
| 3,596,927 | 8/1971 | Mitchell et al. | 585/665 |
| 3,641,188 | 2/1972 | Yoo et al. | 585/511 |
| 3,655,811 | 4/1972 | Yoo | 585/511 |
| 3,684,739 | 8/1972 | Mottus et al. | 502/117 |
| 3,808,150 | 4/1974 | Yoo | 585/514 |
| 3,816,372 | 6/1974 | Lugli et al. | 534/11 |
| 3,994,945 | 11/1976 | Poggio et al. | 534/11 |
| 4,290,918 | 9/1981 | Bayer et al. | 502/159 |
| 4,444,903 | 4/1984 | Carbonaro et al. | 502/102 |

FOREIGN PATENT DOCUMENTS

| | | |
|---|---|---|
| 907325 | 8/1972 | Canada . |
| 1225559 | 3/1971 | United Kingdom . |
| 1233020 | 5/1971 | United Kingdom . |

OTHER PUBLICATIONS

Jeske et al., J. Am. Chem. Soc., 107, 8091–8103, (1985).
Manriquez et al., J. Am. Chem. Soc., 100, 3939–41, (1978).
Watson, CA 100:23046s, (1985).
Ballard et al., CA 92:94732q, (1980).
Chemical Abstract 97:58090y, (1981).
J. Chem. Soc., Chem. Commun. (1983), pp. 561–563, Peter B. Hitchcock, et al., "Hydrocarbon–soluble, Crystalline, Four–co-ordinate Chloro(aryl oxide)s Dialkylamido(aryl oxide)s, and Di[bis(trimethylsilyl)-cyclopentadienyl's of Th$^{iv}$ and U$^{iv}$; X-Ray Crystal Structure of Diethylamidotris(2,6-di-t-butylphenoxo)uranium (IV)".
Angew. Chem. Int. Ed. Engl., 19(8), (1980), pp. 622–3, Borislav Bogdanovic, et al., "Dimerization of Propylene with Catalysts Exhibiting Activities Like Highly–Active Enzymes".
Organometallics, vol. 2 (1983), pp. 963–996, Teddy H. Cymbaluk, et al., "Synthesis and Characterization of (Pentamethylcyclopentadienyl)uranium Tris(allyl) Complexes".
J.A.C.S., vol. 98 (1976), pp. 703–710, Tobin J. Marks, et al., "Tris($\eta^5$-cyclopentadienyl)alkyl and -alkenyl Compounds of Thorium(IV)".
J.A.C.S., vol. 95 (1973), pp. 5529–5539, Tobin J. Marks, et al., "Synthesis, Chemistry and Spectroscopy of Some Tris(pentahaptocyclopentadienyl)uranium(IV) Alkyl and Aryl Compounds".
J.A.C.S., vol. 103 (1981), pp. 6650–6667, Paul J. Fagan, et al., "Synthesis and Properties of Bis(pentamethylcyclopentadienyl) Actinide Hydrocarbyls and Hydrides, A New Class of Highly Reactive f-Element Organometallic Compounds".
Chem. Abstracts 100:102722n.
Chem. Abstracts 96:198992y.
Chem. Abstracts 91:109728y.
Chem. Abstracts 90:103366m.
Chem. Abstracts 88:190055j.
Chem. Abstracts 88:190054h.
Chem. Abstracts 86:89148a.
Chem. Abstracts 84:30297d.
Chem. Abstracts 79:104656r.
Chem. Abstracts 79:52761z.
Chem. Abstracts 78:29135u.
Chem. Abstracts 74:54350k.
Chem. Abstracts 71:80574u.
Chem. Abstracts 71:38217e.
Chem. Abstracts 74:87315f.
Chem. Abstracts 74:63884q.
Chem. Abstracts 102:25109e.
Chem. Abstracts 88:120589n.
Chem. Abstracts 80:82041c.
Chem. Abstracts 80:14525p.
Chem. Abstracts 79:79239x.
Chem. Abstracts 78:147312x.
Chem. Abstracts 98:34671h.
Chem. Abstracts 78:104164h.
Chem. Abstracts 73:30482h.
Chem. Abstracts 71:61539v.
Chem. Abstracts 83:58971x.
Chem. Abstracts 102:6727p.

*Primary Examiner*—Asok Pal
*Attorney, Agent, or Firm*—Paul D. Hayhurst

[57] ABSTRACT

Uranium di(poly-substituted cyclopentadienyl)-hydride complexes, as well as certain uranium (IV) and rare earth metal complexes, can be employed to catalyze the dimerization of propylene to form selectively 4-methyl-1-pentene.

20 Claims, No Drawings

PROCESS FOR PROPYLENE DIMERIZATION

BACKGROUND OF THE INVENTION

The present invention relates to a process for the dimerization of olefins. More specifically, the invention relates to a new method for the preparation of 4-methyl-1-pentene.

The compound 4-methyl-1-pentene is useful as a monomer or as a comonomer in the production of polyolefins. Typically, 4-methyl-1-pentene is produced via the catalytic dimerization of propylene. Commonly employed catalysts include those containing alkali metals or nickel. Low-selectivity catalysts include thorium nitrate, $WCl_6$, titanium, aluminum alkyls, such as cerium acetylacetonate/aluminum alkyls and certain mixtures of these. Alkali metal catalysts are numerous, but are disadvantageous in that they require high operating temperatures and pressures. Catalysts previously employed for the preparation of 4-methyl-1-pentene via propylene dimerization are all unsatisfactory to the extent that they are not as selective as would be desired. While selectivities to 4-methyl-1-pentene of up to 93 percent have been reported (*Chemical Abstracts*, 100:102722n, using a Na/K-based catalyst), even this is unsatisfactory in view of the difficulty and expense involved in separating 4-methyl-1-pentene from the commonly coproduced $C_6$ olefin and $C_6$ alkane by-products.

U.S. Pat. No. 3,994,945 discloses uranium (IV) tetraallyl compounds and certain halide derivatives thereof. The halide compounds are reported to be useful as catalysts in the stereospecific polymerization of diolefins.

U.S. Pat. No. 3,816,372 discloses uranium (IV) complexes containing metal carbonium $\sigma$ bonds. Ligands such as allyl, cyclobutadienyl and cyclopentadienyl are taught to be coordinated to the metal by $\pi$ bonds. The compounds are disclosed as being useful in the oligomerization of olefins and diolefins, and in the insertion reaction of neutral molecules such as CO and NO.

U.S. Pat. Nos. 3,655,811 and 3,808,150 disclose catalyst compositions consisting essentially of (a) an actinide series metal compound such as thorium nitrate tetrahydrate; (b) a reducing agent; (c) a non-protonic Lewis acid; and as optional, preferred ingredients; (d) a trihydrocarbylphosphine; and (e) an inert, organic solvent. The catalyst composition is disclosed as being useful for catalyzing the polymerization of olefins or phenyl-substituted olefins to normally liquid polymers or oligomers, such as catalyzing the dimerization of propylene. Table II in each of said patents indicates that the catalyst compositions are not selective to 4-methyl-1-pentene.

In view of the deficiencies of prior art methods, it would be desirable to have a process which would provide improved selectivity to 4-methyl-1-pentene.

SUMMARY OF THE INVENTION

The present invention is such a process comprising contacting propylene and a catalyst comprising an element selected from uranium or the rare earth metals under reaction conditions such that 4-methyl-1-pentene is selectively produced. Uranium di(poly-substituted cyclopentadienyl)-hydride complexes are especially selective catalysts. Surprisingly, high selectivity to 4-methyl-1-pentene is obtained using the present invention. The unexpectedly high selectivity advantageously reduces the need for expensive and difficult separation of $C_6$ by-products.

DETAILED DECRIPTION OF THE INVENTION

The process of the present invention advantageously employs a catalyst, propylene and, optionally, a solvent.

Propylene is commercially available, and can be prepared by a number of known methods. In the process of the present invention, propylene can be employed as a gas, a liquid or both.

For the purposes of the present invention, the term "selective" and variations thereof refer to processes which can produce 4-methyl-1-pentene from propylene with a selectivity, as defined hereinafter, of at least 94 mole percent. In the general sense, the term "selectivity" is defined as the moles of 4-methyl-1-pentene in the product stream divided by the total number of moles of reaction products in the reactor effluent stream. Selectivity can also be measured with respect to other $C_6$ olefins or with respect to all $C_6$ compounds in the product stream. High selectivity with respect to other $C_6$ olefins is especially important as the separation of other $C_6$ olefins from 4-methyl-1-pentene is the most difficult separation involved in recovering 4-methyl-1-pentene from the product stream.

The process of the present invention advantageously employs a catalyst comprising at least one element selected from uranium or the rare earth metals. For the purposes of the present invention the rare earth metals include elements having atomic numbers from 57 through 71, i.e., lanthanum, cerium, praseodymium, neodymium, promethium, samarium, europium, gadolinium, terbium, dysprosium, holmium, erbium, thulium, ytterbium and lutetium. Catalysts comprising U, La or Nd are preferred. Mixtures of catalytic metal elements can be employed. Preferred catalysts to be employed in the process of the present invention include uranium or rare earth metal di(poly-substituted cyclopentadienyl)-hydride complexes. The poly-substituted cyclopentadienyl ligands can bear a wide variety of substituents so long as the resulting ligand is substantially inert with respect to propylene, and so long as the substituents are of sufficient size to provide sufficient steric hindrance to make the catalyst composition capable of selectively producing 4-methyl-1-pentene from propylene. More preferred catalysts are represented generally by the formula:

$$[(Cp^*)_2—M^{+x}—H_{(x-2)}]_y$$

wherein Cp* is a poly-substituted cyclopentadienyl ligand, M is a metal selected from the group consisting of uranium and elements having atomic numbers 57 through 71, x can be 3 or 4 and represents the valence of the metal M, and y can be 1 or 2. Preferably, each Cp* independently is a moiety of the formula:

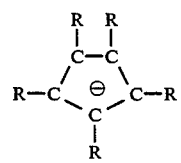

wherein each R independently is H, alkyl of up to about 6 carbon atoms or alkyl substituted silyl such as trimethylsilyl, triethylsilyl, and the like, with the proviso that at least about two R moieties are not H. Preferably, each R is methyl. Y preferably is 2. Examples of catalysts which can be employed in the process of the present invention include bis-(pentahaptotetramethylcyclopentadienyl) uranium hydride, bis-(pentahaptobutyltetramethylcyclopentadienyl) uranium hydride, bis-(pentahaptoethyltetramethylcyclopentadienyl) uranium dihydride, bis-(pentahaptopentamethylcyclopentadienyl) uranium hydride, bis-(pentahapto-bis-(trimethylsilyl)cyclopentadienyl) uranium hydride, bis-(pentahaptopentamethylcyclopentadienyl) neodymium hydride, and bis-(pentahaptopentamethylcyclopentadienyl) lanthanum hydride. Bis-(pentahaptopentamethylcyclopentadienyl) uranium hydride is known to exist as a dimer (M =U, y =2) in which the uranium is present as an equilibrium mixture of the +3 and +4 valences. Accordingly, the number of hydride ligands can equal 1 and 2 for this compound:

$$Cp*_2UH_2]_2 \rightleftharpoons [Cp*_2UH]_2 + \tfrac{1}{2}H_2$$

The most preferred catalyst is bis-(pentahaptopentamethylcyclopentadienyl) uranium hydride.

The preparation of bis-pentamethylcyclopentadienyl uranium alkyls and hydride is reported in *J.A.C.S.* by Juan M. Manriquez, et al., Vol. 100, pp. 3939–3941 (1978). The preparation of di-(bis(trimethylsilyl)cyclopentadienyl) uranium dichloride and di-(bis(trimethylsilyl)cyclopentadienyl) uranium dialkyls are reported by Peter B. Hitchcock et al. in *J. Chem. Soc., "Chem. Commun.,"* pp. 561–563 (1983). The preparation of bis-(pentamethylcyclopentadienyl) neodymium hydride and bis-(pentamethylcyclopentadienyl) lanthanum hydride are reported in *J.A.C.S.*, by Gerald Jeske et al., Vol. 107, pp 8091–8103 (1985).

The catalyst can be prepared as described hereinabove or, alternatively, the active catalyst of the present invention can be generated in situ by subjecting a solution of a uranium di(poly-substituted-cyclopentadienyl) complex to gaseous hydrogen in order to pre-form the hydride catalyst. After removal of the unreacted hydrogen, the catalyst solution is contacted with propylene. Preferred catalyst compositions for this in situ catalyst generation can be represented by the formula:

$$(Cp*_2)MR'_x$$

wherein each R' independently can be a hydrocarbon moiety or a silicon-containing hydrocarbon moiety; and M, x and Cp* are as described previously. Most preferably, Cp* is pentahaptopentamethylcyclopentadienyl.

The term "hydrocarbon" is well known to those skilled in organic chemistry and refers to a moiety or compound consisting essentially of atoms of carbon and hydrogen. Hydrocarbon moieties can be aromatic or aliphatic; can be saturated or unsaturated; can have carbon chains which are branched, cyclic or straight, and can have mixtures of these attributes. Preferred hydrocarbon moieties have up to about 20 carbon atoms and include alkyl, alkenyl, aryl, alkaryl or aralkyl. Examples of hydrocarbon moieties include methyl, ethyl, butyl, phenyl, allyl, benzyl and the like. Lower alkyl and lower alkenyl of up to about 6 carbon atoms are more preferred.

The term "silicon-containing hydrocarbon" refers to hydrocarbons which contain at least one atom of silicon. Examples of silicon-containing hydrocarbon moieties include trimethylsilyl methyl, bis-(trimethylsilyl methyl) and the like.

It is preferred that the catalyst be employed in a substantially inert environment, i.e., an environment having propylene as essentially the only reactive component of a feed stream. The catalyst of the present invention is, in its purified form, sensitive to air, water and other materials which provide a source of acidic protons. Accordingly, it is preferred that the catalyst compositions of the present invention be maintained in an environment which is substantially inert with respect to degradation of the catalyst. This proviso does not apply to the presence of propylene.

The catalyst is employed in a catalytic amount. Typically, from about $1 \times 10^{-5}$ to about $1 \times 10^{-1}$ weight parts catalyst are employed per weight part propylene. Preferably, from about $1 \times 10^{-4}$ to about $1 \times 10^{-2}$ weight parts catalyst are employed per weight part propylene.

A solvent is optionally employed in the process of the present invention. The function of the solvent is to assist in the dissolution of the catalyst, or to function as a reaction medium for the in situ formation of the active catalyst by hydrogenation of an alkyl-containing precursor. Examples of typical solvents include saturated hydrocarbons, such as pentane, hexane, heptane, octane and other normal or branched saturated paraffins; aromatic hydrocarbons, such as benzene, xylene and other alkyl benzenes; cyclic saturated hydrocarbons, such as cyclopentane, cyclohexane and the like as well as mixtures thereof. Liquid propylene can be employed as a solvent. Toluene is the preferred solvent. The amount of solvent can be varied widely. Typically, from about 5 to about 50 weight parts of solvent are employed per weight part of propylene.

The process of the present invention can be operated at any combination of temperature and pressure at which 4-methyl-1-pentene is selectively produced. Typically, the process is conducted at a temperature ranging from just above the freezing point of the reaction mixture to just below the temperature at which the catalyst decomposes. Preferably, the temperature is from about 10° C. to about 180° C. In general, the reaction proceeds more slowly at lower temperatures. Typically, the process is conducted at a pressure of from about 1 to about 500 atmospheres. In general, the reaction proceeds faster as the pressure increases. The reaction rate is a function of temperature, pressure, catalyst concentration, propylene concentration and the like.

When propylene and a catalyst are contacted under reaction conditions as described hereinabove, 4-methyl-1-pentene is selectively produced. Typically, the selectivity is at least about 94 mole percent, preferably is at least about 96 mole percent, more preferably is at least about 98 mole percent and most preferably is greater than 99 mole percent. This selectivity can be overall selectivity, i.e., based on all products produced, or it can be selectivity with respect to $C_6$ alkanes or with respect to $C_6$ olefins, or all $C_6$ compounds.

SPECIFIC EMBODIMENTS OF THE INVENTION

The following examples are given to illustrate the invention and should not be construed as limiting its scope. All parts and percentages are by weight unless otherwise indicated. Cp* represents the pentamethylcyclopentadienyl moiety in the examples.

EXAMPLE 1

A 100 ml stainless steel bomb is taken into an argon-filled inert atmosphere drybox (<0.2 ppm $O_2$) and into the bomb are placed a Teflon®-coated magnetic stir-bar, 15.9 mg of $(UCp*_2H_2)_2$, and 25.0 $\mu l$ each of heptane and 2,2-dimethylbutane (GC internal standards). The bomb is sealed, is removed from the inert atmosphere box and the temperature is maintained at 25° C. Liquid propylene (23 g, 45 ml), which is purified in order to remove oxygen, water and other detrimental species, is added to the bomb. Catalysts which can be employed to remove water, oxygen and other paramagnetic impurities are well known in the art, and include such materials as molecular sieves, alumina, silica and finely divided copper on an alumina matrix, such as Dow Q1® catalyst, available from The Dow Chemical Company.

The contents of the bomb are magnetically stirred for 72 hours at 25° C. After 72 hours, the bomb is vented and the contents are analyzed by gas chromatography using a Hewlett-Packard 5880 GC with a 60 meter J & W Narrow Bore Capillary Column bonded with DB-1. The analysis shows 737.2 turnovers (moles of product/moles of uranium) to 4-methyl-1-pentene. The overall selectivity to 4-methyl-1-pentene is 97.84 percent. The major by-products are easily separated $C_9$'s (1.774 percent). The selectivity to 4-methyl-1-pentene with respect to other $C_6$'s is 99.611 percent.

EXAMPLE 2

The procedure is identical to that of Example 1 except that the reaction is allowed to proceed at 40° C. for 168 hours and 5.9 mg of $(UCp*_2H_2)_2$ is employed. Analysis by gas chromatography shows a total of 3149.9 turnovers to 4-methyl-1-pentene with an overall selectivity of 95.27 percent and a selectivity to 4-methyl-1-pentene with respect to other $C_6$'s of 99.642 percent.

EXAMPLE 3

The procedure is identical to that of Example 1 except that the reaction is allowed to proceed at 10° C. for 72 hours and 9.7 mg of $(UCp*_2H_2)_2$ is employed. Analysis by gas chromatography shows a total of 416.9 turnovers to 4-methyl-1-pentene with an overall selectivity of 98.16 percent and a selectivity to 4-methyl-1-pentene with respect to other $C_6$'s of 99.403 percent.

EXAMPLE 4

The procedure is identical to that of Example 1 except that the reaction is allowed to proceed at 55° C. for 72 hours and 10.5 mg of $(UCp*_2H_2)_2$ is employed. Analysis by gas chromatography shows a total of 1925.3 turnovers to 4-methyl-1-pentene with an overall selectivity of 95.24 percent and a selectivity to 4-methyl-1-pentene with respect to other $C_6$'s of 99.561 percent.

EXAMPLE 5

The procedure is identical to that of Example 1 except that 5.0 ml of toluene is added to the bomb in the drybox as a solvent and the reaction is allowed to proceed at 60° C. for 15 hours, and 12.0 mg of $(UCp*_2H_2)_2$ is employed. Analysis by gas chromatography of the reaction products shows a total of 404.6 turnovers with an overall selectivity to 4-methyl-1-pentene of 97.46 percent and a selectivity to 4-methyl-1-pentene with respect to other $C_6$'s of 99.440 percent.

EXAMPLE 6

The procedure is identical to that of Example 1 except that 11.0 mg of $NdCp*_2H$ is employed as the catalyst and the reaction is allowed to proceed at 40° C. for 18 hours. After cooling and venting, the contents of the bomb are analyzed using capillary gas chromatography. Analysis by gas chromatography shows a total of 3.7 turnovers with an overall selectivity of 31.88 percent and a selectivity with respect to other $C_6$'s of 91.259 percent.

EXAMPLE 7

A 100 ml stainless steel bomb is taken into an argon-filled inert atmosphere drybox (<0.2 ppm $O_2$) and into it is placed a Teflon-coated magnetic stir-bar, 10.4 mg of $(UCp*_2H_2)_2$, 5.0 ml of toluene and 25.0 $\mu l$ of heptane (GC internal standard). The bomb is sealed, removed from the inert atmosphere box and heated to 25° C. The bomb is charged with 125 psig of propylene gas at 25° C., then sealed and heated to 60° C. for a total of 15 hours. The bomb is then cooled, vented, opened and the contents are analyzed by capillary gas chromatography. The analysis reveals the formation of 4-methyl-1-pentene with a catalyst efficiency of 421.2 turnovers and an overall selectivity to 4-methyl-1-pentene of 96.71 percent. The selectivity with respect to other $C_6$'s is 99.644 percent.

EXAMPLE 8

A 300 ml stainless steel bomb is taken into an argon-filled inert atmosphere drybox (<0.2 ppm $O_2$) and into it is placed 156.6 mg of $UCp*_2(CH_3)_2$, 50 ml of toluene, and 500 $\mu l$ of cyclohexane (GC internal standard). The bomb is sealed, removed from the drybox and charged with 600 psig of hydrogen gas to form the catalyst in situ. The solution is stirred at room temperature for 2 hours, after which time the hydrogen is vented. The bomb is then charged with 200 ml of liquid propylene and is heated to 50° C. Samples are taken periodically for capillary GC analysis. The analysis reveals the formation of 4-methyl-1-pentene with an initial rate of about 70 turnovers per hour and a total of 2901 turnovers after 136.1 hours. The overall selectivity is 94.3 percent and the selectivity with respect to other $C_6$'s is 99.3 percent.

EXAMPLE 9

The procedure is identical to that of Example 8 except that 155.2 mg of $UCp*_2(CH_3)_2$ is used to form the catalyst in situ and the reaction is allowed to proceed at 25° C. Samples taken for analysis reveals the formation of 4-methyl-1-pentene with an initial rate of about 40 turnovers per hour and a total of 1,925 turnovers after 302 hours. The overall selectivity is 96.3 percent and the selectivity with respect to other $C_6$'s is 99.3 percent.

EXAMPLE 10

The procedure is identical to that of Example 8 except that 31.2 mg of uranium bis-(1,3-bis-trimethylsilyl-cyclopentadiene) bis-trimethylsilylmethyl is used, 500 $\mu l$ heptane is used for the GC internal standard, and the reaction is allowed to proceed at 50° C. for 22.5 hours. GC analysis shows the formation of 4-methyl-1-pentene.

EXAMPLE 11

A 100 ml flask is charged with 20 mg of Cp*$_2$La(CH(SiMe$_3$)$_2$). Hydrogen gas is admitted to the flask at 1 atmosphere pressure, and the solid is allowed to stand at room temperature overnight in the presence of hydrogen. The hydrogen is then removed and 5 ml of toluene is added, followed by propylene gas in an amount sufficient to bring the pressure in the flask to 1 atmosphere, gauge. The mixture is allowed to stir for 16 hours. Capillary GC analysis of the reaction mixture shows the presence of 4-methyl-1-pentene.

What is claimed is:

1. A process for the preparation of 4-methyl-1-pentene, the process comprising contacting propylene and a catalyst comprising uranium under reaction conditions to produce 4-methyl-1-pentene with a selectivity of at least 94 mole percent with respect to other C$_6$ olefins.

2. The process of claim 1 wherein the selectivity with respect to other C$_6$ olefins is at least about 96 mole percent.

3. The process of claim 1 wherein the selectivity with respect to other C$_6$ olefins is at least about 98 mole percent.

4. The process of claim 1 wherein the selectivity with respect to other C$_6$ olefins is at least about 99 mole percent.

5. A process comprising contacting propylene and a catalyst comprising uranium under reaction conditions to product 4-methyl-1-pentene with a selectivity with respect to all C$_6$ compounds of at least 94 mole percent.

6. The process of claim 5 wherein the selectivity with respect to all C$_6$ compounds is at least about 96 mole percent.

7. The process of claim 5 wherein the selectivity with respect to all C$_6$ compounds is at least about 98 mole percent.

8. The process of claim 5 wherein the selectivity with respect to all C$_6$ compounds is at least about 99 mole percent.

9. The process of claim 5 wherein the overall selectivity of 4-methyl-1-pentene is at least 94 mole percent with respect to all products of the process.

10. The process of claim 9 wherein the overall selectivity is at least about 96 mole percent.

11. A process for the selective preparation of 4-methyl-1-pentene, the process comprising contacting propylene and a catalyst comprising a uranium di(poly-substituted cyclopentadienyl)-hydride complex under reaction conditions to produce 4-methyl-1-pentene.

12. A process comprising contacting propylene with a catalyst selected from the group consisting of:
   (a) a uranium (III)-di(poly-substituted cyclopentadienyl)-hydride complex;
   (b) a uranium (IV)-di(poly-substituted cyclopentadienyl)-dihydrogen complex; and
   (c) a uranium (III) or uranium (IV) di(poly-substituted cyclopentadienyl)-alkyl complex, and the active catalyst is prepared in situ by subjecting the alkyl complex to gaseous hydrogen in order to preform the hydride catalyst;
under reaction conditions to produce 4methyl-1-pentene.

13. The process of claim 12 wherein the selectivity to 4-methyl-1-pentene is at least 94 mole percent.

14. The process of claim 13 wherein each poly-substituted cyclopentadienyl moiety is represented by the formula:

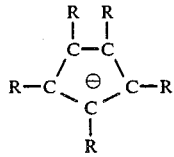

wherein each R independently is H, alkyl of up to about 6 carbon atoms or alkyl substituted silyl with the proviso that at least about 2 R moieties are not H.

15. The process of claim 14 wherein each R is methyl or H, with the proviso that at least 2 R moieties are methyl.

16. A process for the selective preparation of 4-methyl-1-pentene, the process comprising contacting propylene with a catalyst of the formula:

$$[(Cp*)_2 - M^{+x} - H_{(x-2)}]_y$$

wherein Cp* is pentahaptopentamethylcyclopentadienyl, X equals 3 or 4, M is U, and y is 1 or 2, the contacting being in a substantially inert environment at a temperature of from about 10° C. to about 180° C.

17. The process of claim 16 wherein x is 3.

18. The process of claim 16 wherein x is 4.

19. The process of claim 16 wherein the contacting is conducted in the presence of a substantially inert solvent.

20. The process of claim 16 wherein the overall selectivity to 4-methyl-1-pentene is at least 94 mole percent.

* * * * *